(12) United States Patent
Price

(10) Patent No.: US 11,998,652 B2
(45) Date of Patent: Jun. 4, 2024

(54) FOGGER DISINFECTANT DEVICE

(71) Applicant: Susan Coats Price, Mount Olive, NC (US)

(72) Inventor: Susan Coats Price, Mount Olive, NC (US)

(*) Notice: Subject to any disclaimer, the term of this patent is extended or adjusted under 35 U.S.C. 154(b) by 694 days.

(21) Appl. No.: 17/166,129

(22) Filed: Feb. 3, 2021

(65) Prior Publication Data

US 2022/0072173 A1 Mar. 10, 2022

Related U.S. Application Data

(60) Provisional application No. 63/076,088, filed on Sep. 9, 2020.

(51) Int. Cl.
| *A61L 2/22* | (2006.01) |
| *A01N 27/00* | (2006.01) |
| *A01N 31/02* | (2006.01) |
| *A01N 33/08* | (2006.01) |
| *A01N 33/12* | (2006.01) |
| *A61L 2/26* | (2006.01) |
| *A61L 101/02* | (2006.01) |
| *A61L 101/34* | (2006.01) |
| *A61L 101/50* | (2006.01) |

(52) U.S. Cl.
CPC ............... *A61L 2/22* (2013.01); *A01N 27/00* (2013.01); *A01N 31/02* (2013.01); *A01N 33/08* (2013.01); *A01N 33/12* (2013.01); *A61L 2/26* (2013.01); *A61L 2101/02* (2020.08); *A61L 2101/34* (2020.08); *A61L 2101/50* (2020.08); *A61L 2202/14* (2013.01); *A61L 2202/15* (2013.01); *A61L 2202/25* (2013.01)

(58) Field of Classification Search
CPC .......... A61L 2/22; A61L 2/26; A61L 2101/34; A61L 2101/02; A61L 2101/50; A61L 2202/14; A61L 2202/15; A61L 2202/25; A01N 33/02
See application file for complete search history.

(56) References Cited

U.S. PATENT DOCUMENTS

| 2004/0213750 | A1* | 10/2004 | Bennett | A01N 31/02 |
| | | | | 514/724 |
| 2021/0338872 | A1* | 11/2021 | Krawczyk | A61L 2/26 |
| 2022/0062479 | A1* | 3/2022 | Crook | A01N 33/12 |

* cited by examiner

*Primary Examiner* — Lessanework Seifu
(74) *Attorney, Agent, or Firm* — Brennan, Manna & Diamond, LLC

(57) ABSTRACT

This present invention relates to a portable fogger disinfectant device which is used to disperse a novel disinfecting and sanitizing solution and related propellant to disinfect a room or other enclosed space. The spray material is stored in a pressure-activated cylinder with a nozzle, a sensor and a timer. In one embodiment, the disinfecting and sanitizing solution is comprised of an ethanol, an alkyl comprised of C14, C12, and C16, water as a base for other ingredients, fragrance oils, ethanolamine, a propellant and an ammonium hydroxide.

11 Claims, 4 Drawing Sheets

FOGGER DISINFECTANT DEVICE

CROSS-REFERENCE TO RELATED APPLICATION

The present application claims priority to, and the benefit of, U.S. Provisional Application No. 63/076,088, which was filed on Sep. 9, 2020 and is incorporated herein by reference in its entirety.

FIELD OF THE INVENTION

The present invention relates generally to the field of disinfection sprayer devices. More specifically, the present invention relates to a single use aerosol type fogger disinfectant device for releasing a novel and airborne disinfecting and sterilizing solution to eliminate bacteria, viruses, germs, fungi and other pathogens within a confined or semi-confined area, such as a room in a home, daycare center, school, hospital, restaurant, office, dormitory, etc. Accordingly, the present specification makes specific reference thereto. However, it is to be appreciated that aspects of the present invention are also equally amenable to other like applications, devices and methods of manufacture.

BACKGROUND OF THE INVENTION

Bacterial and microbial contamination of rooms, offices, daycare centers, restaurants, schools, treatment rooms, hospitals, hotels, airports, and other confined spaces has long been a problem, and presents a risk of infection and transmission of diseases for humans. More specifically, bacteria, viruses, germs, and other disease-causing microbes adhere to surfaces after contact with humans, and also linger in the air within a room after being discharged by, for example, a person sneezing, speaking or coughing. In this way, humans have spread infectious diseases among each other since time immemorial, including the common cold, influenza, rotavirus, hepatitis A, tuberculosis, conjunctivitis, staphylococcal bacterial infections, COVID, strep throat and other streptococcal bacterial infections. Therefore, eliminating or reducing the potential for disease transmission is a major concern for all individuals, as well as the operators of businesses, hospitals, hotels, airports, and the like.

In an effort to address such concerns and to maintain a properly sterilized environment, manual labor is oftentimes required by maintenance and other custodial staff. More specifically, these individuals spend a considerable amount of time cleaning and disinfecting homes, offices, schools, restaurants, business areas and other enclosed spaces. However, manually cleaning every surface is time consuming, tiring, ineffective and may result in some spots being left unclean which, in turn, can lead to the spread and transmission of harmful germs, bacteria, microbes, viruses, and the like. For example, with manual cleaning and sanitizing attempts, it is also difficult to ensure high-level disinfection and sanitization due to a number of challenges. These challenges include missed areas, re-contamination from dirty sponges, rags and mops, and improper use and mixing of antibacterial cleaning solutions.

Further, examining rooms, visiting rooms, surgical rooms and patient rooms are very expensive to operate and maintain, and most hospitals and clinics seek to utilize these spaces to the maximum extent possible. With high patient turnover rates, there is a constant pressure on cleaning and custodial staff to prepare each of the rooms and restore them to the required sanitized and disinfected condition as quickly as possible, and before the next patient is handled or visitor received. This effort is labor intensive and can still result in some surfaces in the area of concern remaining untreated given the time constraints and the fact that it is not possible for the staff to visibly see which surfaces have been cleaned, and which ones have not. Similar challenges exist in the non-medical environment, such as with restaurants, office spaces, hotels, airports and the like, wherein custodial staff must expend significant time and labor to disinfect such spaces and the contents placed therein.

Additionally, according to the Centers for Disease Control and Prevention ("CDC"), approximately two million people become sick each year due to infections caused by antibiotic-resistant bacteria, and at least 23,000 people die as a direct result of those infections. Further, many individuals who officially succumb to other conditions do so after their health has been compromised by an antibiotic-resistant infection. Overuse of antibiotics is a major factor in the increase in antibiotic resistance, and can be addressed in part by taking steps to eliminate or at least reduce the presence of germs, bacteria, viruses, and other infectious agents before they get the chance to cause illness or come into contact with a new human host.

Therefore, there exists a long felt need in the art for a fogger disinfectant device that can be employed within homes, businesses, restaurants, schools, hospitals, hotels, airports, and the like to effectively and efficiently disinfect and sanitize an enclosed area, and all of the objects placed therein in a single operation. There is also a long felt need in the art for a fogger disinfectant device having a novel disinfecting and sanitizing solution that eliminates 99.9% of the germs, bacteria, viruses, microbes, and the like present in the treated area, and that leaves a pleasant odor post cleaning Moreover, there is a long felt need in the art for a disinfecting device that substantially reduces the amount of manual labor and time required to properly disinfect and sanitize an enclosed space, thereby freeing up the time of the cleaning staff for other tasks and allowing the enclosed space to be returned to productive use more quickly. Finally, there is a long felt need in the art for a disinfecting device that is relatively inexpensive to manufacture and is both safe and easy to use.

The subject matter disclosed and claimed herein, in one embodiment thereof, comprises a fogger disinfectant device comprised of a pressurized cylinder containing a propellant, a novel disinfecting and sanitizing solution, and a nozzle having an opening therein that, when activated, is in fluid communication with the pressurized contents of the cylinder to release the same into an enclosed space. The fogger disinfectant device of the present invention kills bacteria, viruses and the like, eliminates odors, is gluten free, and does not require a rinse or wipe down of the treated area post treatment. In this manner, the fogger disinfectant device of the present invention accomplishes all of the forgoing objectives, and provides a relatively safe, easy, convenient and cost-effective solution.

SUMMARY OF THE INVENTION

The following presents a simplified summary in order to provide a basic understanding of some aspects of the disclosed innovation. This summary is not an extensive overview, and it is not intended to identify key or critical elements or to delineate the scope thereof. Its sole purpose is to present some general concepts in a simplified form as a prelude to the more detailed description that is presented later.

The subject matter disclosed and claimed herein, in one embodiment thereof, comprises an aerosol fogger disinfectant device that offers complete coverage within the enclosed space in which it is activated. More specifically, the fogger disinfectant device of the present invention utilizes a pressure-activated cylinder that contains a disinfecting and sterilizing solution, and a nozzle having a spray opening that, upon activation, releases the disinfecting and sterilizing solution throughout an entire room. To activate the fogger disinfectant device, the nozzle is pushed downwards (i.e., in the direction of the cylinder) using a flap present on the nozzle head, thereby allowing the disinfecting and sterilizing solution to be released from the pressurized cylinder through the opening in the nozzle. As the solution leaves the nozzle spray opening, the same is propelled in an upward and outward direction to disinfect the entire room and the enclosed space at the same time.

The disinfecting and sterilizing solution of the present invention is a novel mix of ethanol, alkyl, ammonium saccharinate such as dimethyl benzyl ammonium saccharinate, water, fragrant oils, and a propellant such as butane, propane or compressed air. Additional ingredients may also be used in the disinfecting solution formulation including, without limitation, ammonium hydroxide, one or more essential fragrance oils such as *Cymbopogon martini* oil (palmarosa), *Eucalyptus globulus* leaf oil, *Pogostemon cablin* oil (patchouli), *Lavandula angustifolia* oil (lavender), *Pelargonium graveolens* extract (geranium), *Vanilla planifolia* flower extract, and *Coriandrum sativum* fruit oil (coriander).

In one embodiment of the present invention, the disinfectant material kills 99.9% of the contacted germs, bacteria and the like using a composition comprising approximately 60% Ethanol, 0.3% Alkyl (comprised of 60% C14, 20% C12, and 20% C16), 10% water, 20% fragrance oils, 4-5% ethanolamine, 4-5% ammonium hydroxide, propellant and other ingredients (all percentages are by volume). The fogger of the present invention is easily portable and has an industrial-strength metal nozzle that does not wear out over time, and that maintains consistent mist droplet size. The nozzle is optimized for the radial and vertical distribution of the disinfectant, and is capable of broadcasting the disinfectant onto the surfaces within the room in an arch like pattern to ensure equal spread or dispersal of the disinfecting solution.

In a further embodiment of the present invention, the disinfectant material used in the fogger disinfectant has a composition comprising approximately 55% ethanol, 0.5% alkyl (comprised of 50% C14, 30% C12, and 20% C16), 15-17% water, 18-20% fragrance oils using components such as eenzyl acetate, eugenol, floral pyranol, *Lavandula angustifolia* oil, *Pogostemon cablin* oil and the like, 3-4% ethanolamine, and 3-4% ammonium hydroxide and propellant and other ingredients. The formulation kills germs and odor causing bacteria on all types of surfaces, prevents mold and mildew build-up, and results in a fragrant scent post cleaning.

In yet a further embodiment of the present invention, the disinfectant solution has a composition comprising of approximately 60% ethanol, 0.09% alkyl dimethyl benzyl ammonium saccharinate, 20% water as a base for other ingredients, 18% fragrance oils or perfume, and 1.91% ammonium hydroxide. In this particular embodiment, the propellant is not a part of the formulation/composition.

In another embodiment of the present invention, a method of quickly disinfecting and sanitizing a room or an enclosed space, such as a restaurant, business area, home, hospital, school, hotel, airport, daycare center, and the like, to remove bacteria, germs, viruses and microbiological contamination is disclosed. The method includes the step of initially acquiring a fogger disinfectant device of sufficient capacity to disperse a disinfecting and sanitizing solution onto substantially all of the surfaces in the room or enclosed space. Next, the disinfecting fogger device is placed substantially in the center of the room, and at a height that is appropriate for allowing the dispersed solution to reach all surfaces. The nozzle of the fogger device is then activated by pressing down the nozzle using a flap present on the nozzle head. The fogger device is allowed sufficient time to discharge the disinfectant material, and thereafter allows time for the disinfectant to contact the surfaces in the room. Finally, the method ends by returning the room to productive use once the disinfecting solution has sufficiently dried.

A yet another embodiment of the present invention, a device for dispensing a disinfecting solution to the surroundings is disclosed and comprises a pressure-activated cylinder configured to contain a propellant and a novel disinfecting solution. More specifically, the device comprises a diffusing nozzle which is coupled to the cylinder to release the disinfecting solution and the propellant through an opening at the top of the nozzle once activated. The nozzle present on the top of the cylinder is activated by pressing the nozzle down towards the cylinder to release the disinfectant from the cylinder in an upward and 360 degree outwardly direction. The pressure of the cylinder is predetermined, and is configured for a conventional space. The disinfecting solution of the fogger disinfectant device preferably has a composition of approximately 60% ethanol, 0.3% alkyl (comprised of 60% C14, 20% C12, and 20% C16), 10-12% water as a base for other ingredients, 20% fragrance oils, 4% ethanolamine, and 5% ammonium hydroxide, propellant and other ingredients. In one embodiment, propanol or isopropanol may be used in place of ethanol. Further, the propellant may be a liquified hydrocarbon which is insoluble in the solution.

In yet a further embodiment of the present invention, the liquid disinfecting composition may comprise approximately 70% weight by volume (w/v) ethyl alcohol, 5% w/v propylene glycol, 0.8% diethyl phthalate to denature alcohol, 10% fragrance oils and 14.2% water in addition to the propellant to form an aerosol spray. Further, the nozzle may be adjustable to provide different dispersal patterns, and/or comprise one or more interchangeable screens to control droplet size, wherein the droplet size preferably ranges from between about 5 and 50 microns. Alternatively, the disinfecting solution may comprise between 60 and 70% weight by volume of an alcohol, propylene glycol, diethyl phthalate, fragrance oils and water.

In each of the embodiments described herein, the disinfecting solution/material should be optimized to exhibit relatively fast drying characteristics, thereby providing dry surfaces within a relatively short time following the activation of the disinfecting fogger device and allowing the room or other enclosed space to be quickly returned to productive use.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
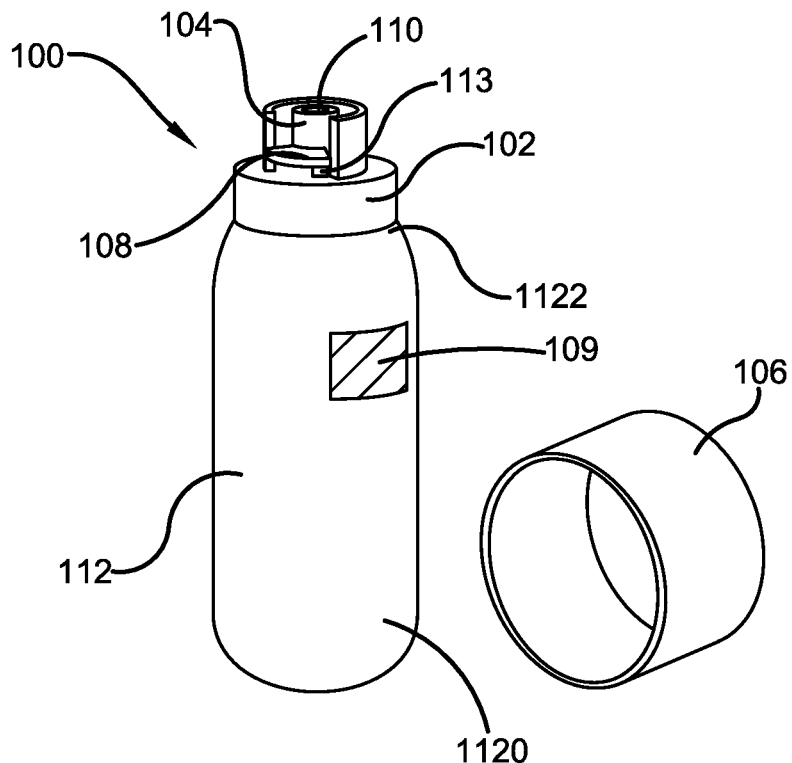
FIG. 1 illustrates a perspective view of one potential embodiment of the fogger disinfectant device of the present invention in accordance with the disclosed architecture and with its cap removed.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

Referring initially to the drawings, FIG. 1 illustrates a perspective view of one potential embodiment of the fogger disinfectant device 100 of the present invention in accordance with the disclosed architecture and with its cap 106 removed. More specifically, the portable device 100 comprises a housing or cylinder 112 having a base 1120 and a collar 1122, wherein the cylinder 112 contains a disinfecting solution 200 under a pressure that is greater than the ambient pressure or the room pressure. The fogger device 100 is further comprised of a nozzle 104 with a flap 108 and a spray opening 110 that is positioned on top of the nozzle 104. The nozzle 104 is coupled to the cylinder 110 through a nozzle cap 102, and is in fluid communication with an interior of the cylinder 112 when activated. The nozzle 104 is moved to an open or activated position by removing the cap 106 of the fogger 100, and pressing the flap 108 in a downward direction towards the cylinder 112, thereby facilitating the release of the disinfecting solution 200 (which is under pressure) from the cylinder 112 through the nozzle opening or orifice 110. In this manner, the disinfecting solution 200 stored inside the cylinder 112 is distributed evenly around the room to disinfect the room.

Figure 2:
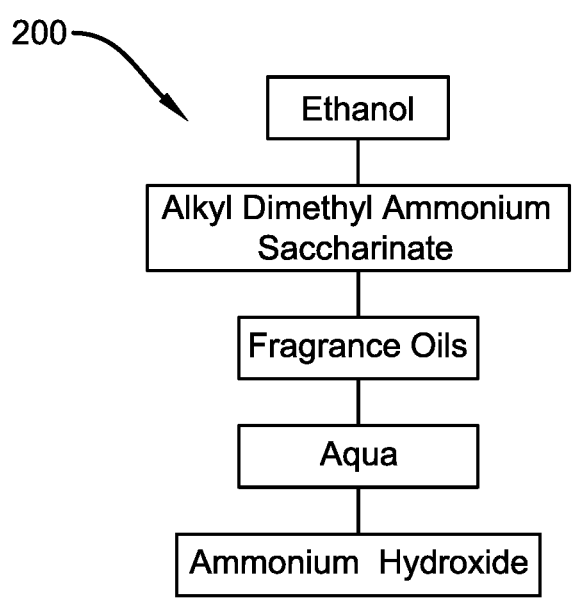
FIG. 2 illustrates a diagrammatic representation of one potential formulation of the disinfecting and sanitizing solution for use in the fogger disinfection device of the present invention in accordance with the disclosed architecture.

The cylinder 112 itself may be made out of a non-elastic and non-oxidizing material, such as a metal, alloy, glass, or similar type material. The cylinder 112 has a volume and is configured to store a predetermined amount of disinfecting solution 200 and a propellant at a predetermined pressure that is greater than the ambient pressure. In one embodiment, the volume of the cylinder 112 is in the range of about 500 ml to about 2,250 ml, though the precise volume will depend on the size of the room or enclosed area to be disinfected and sanitized. For example, in one embodiment, the fogger device 100 may offer coverage to an approximately 700-square foot area. In an alternative embodiment, the fogger device 100 may offer coverage to an approximately 1,000-square foot area. Nonetheless, the coverage is not so limited, and the fogger device 100 may be designed for larger or smaller coverage areas as well, as per the needs and preferences of the user. The pressure in which the disinfecting solution 200 and propellent are stored within the cylinder 112 is in the range of about 3 bar to about 15 bar FIG. 2 illustrates a diagrammatic representation of one potential formulation of the disinfecting and sanitizing solution 200 for use in the fogger disinfection device 100 of the present invention in accordance with the disclosed architecture. While a number of potential formulations are disclosed herein, the composition of the disinfecting solution 200 preferably comprises about 60% ethanol, 0.09% alkyl dimethyl benzyl ammonium saccharinate, 20% water as a base for other ingredients, 18% fragrance oils or perfume, and 1.91% ammonium hydroxide by volume. The alkyl dimethyl benzyl ammonium saccharinate may be selected from the group consisting of C14, C12 and C16 dimethyl benzyl ammonium saccharinates. In one embodiment, the alkyl dimethyl benzyl ammonium saccharinate may have approximately 50% C14, 30% C12, and 20% C16 by volume. Alternatively, the alkyl dimethyl benzyl ammonium saccharinate may have 60% C14, 20% C12, and 20% C16 concentration. Alternatively, the percentage of ethanol can be in the range 50-65%, and the percentage of water could be in the range of 15-30% of the disinfecting solution 200.

Ethanol is the preferred co-solvent and enhances the solubility of the quaternary ammonium salt and the fragrances, while also drying quickly. Ethanol also kills germs and microbes on surfaces. The alkyl dimethyl benzyl ammonium saccharinate is antimicrobial, and also actively kills germs, bacteria, viruses, microbes, and the like. Water is used to adjust the concentration of ingredients to deliver targeted benefits, wherein the ammonium hydroxide controls the pH level of the disinfecting solution 200 and ensures stability and maximizes performance. Fragrance oils used in the disinfecting solution 200 may be one or more of a *Cymbopogon martini* oil (palmarosa), *Eucalyptus globulus* leaf oil, *Pogostemon cablin* oil (patchouli), *Lavandula angustifolia* oil (lavender), *Pelargonium graveolens* extract (geranium), *Vanilla planifolia* flower extract, *Coriandrum sativum* fruit oil (coriander), acetyl cedrene, dipropylene glycol, eugenol, linalyl acetate and the like.

Butane or propane may be used as the propellant to disperse the disinfecting material 200 from the cylinder 112. The propellant is preferably inert, and does not form a part of the disinfectant formulation. Nonetheless, the propellant needs to be effective to discharge substantially all of the contents of the cylinder 112 in a relatively short period of time.

Figure 3:
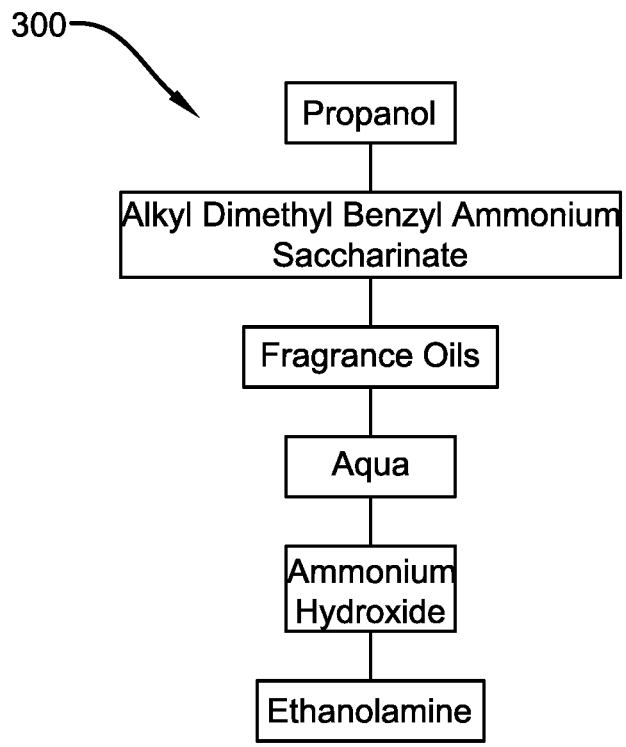
FIG. 3 illustrates a diagrammatic representation of another potential formulation of the disinfecting and sanitizing solution for use in the fogger disinfection device of the present invention in accordance with the disclosed architecture.

FIG. 3 illustrates a diagrammatic representation of another potential formulation of the disinfecting and sanitizing solution 300 for use in the fogger disinfection device 100 of the present invention in accordance with the disclosed architecture. More specifically, the alternative disinfecting solution 300 of the fogger disinfectant device 100 has a composition of approximately 60% propanol, 0.5% alkyl (comprised of approximately 60% C14, 20% C12, and 20% C16), 10% water as a base for other ingredients, 20% fragrance oils, 4% ethanolamine, and 5% ammonium hydroxide.

In one embodiment, isopropanol may be used in place of the propanol. Also, compressed air may be used as the propellant. Alternatively, butane or propane may be used as the propellant, as described above. Nonetheless, it will be appreciated that the composition of the alternative disinfecting and sanitizing solution 300 may have different percentages by volume (or by weight) of the constituents as per the preferences of the user and/or the manufacturer. For example, in a further alternative embodiment, the liquid disinfecting composition 300 comprises approximately 70% weight by volume (w/v) ethyl alcohol, 5% w/v propylene glycol, 0.8% diethyl phthalate to denature alcohol, 10% fragrance oils and 14.2% water in addition to the propellant to form an aerosol spray.

Figure 4:
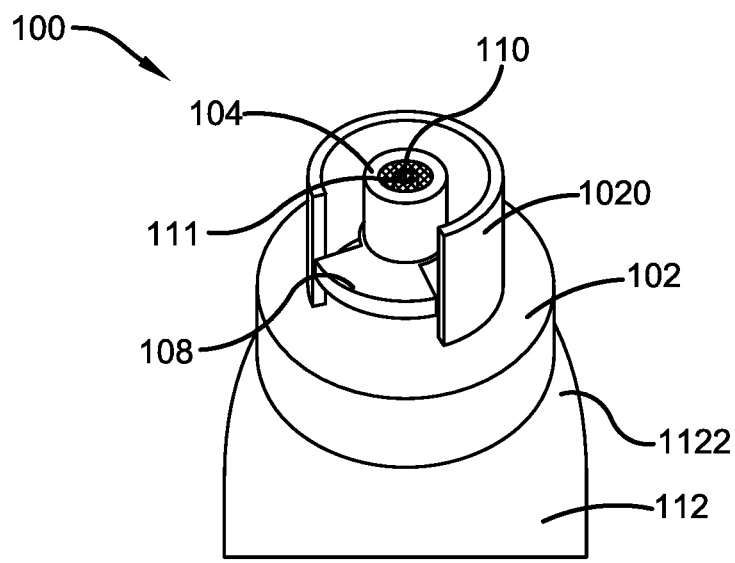
FIG. 4 illustrates a partial perspective view of one potential embodiment of the nozzle of the portable fogger disinfectant device of the present invention in accordance with the disclosed architecture.
Figure 5:
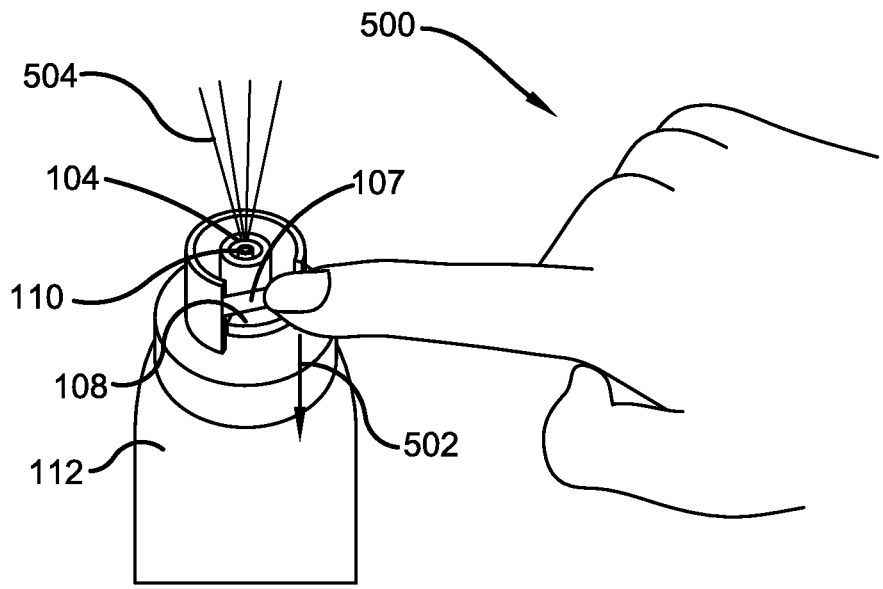
FIG. 5 illustrates a partial perspective view of one potential embodiment of the nozzle of the portable fogger disinfectant device of the present invention in accordance with the disclosed architecture in the process of being activated by a user.
Figure 6:
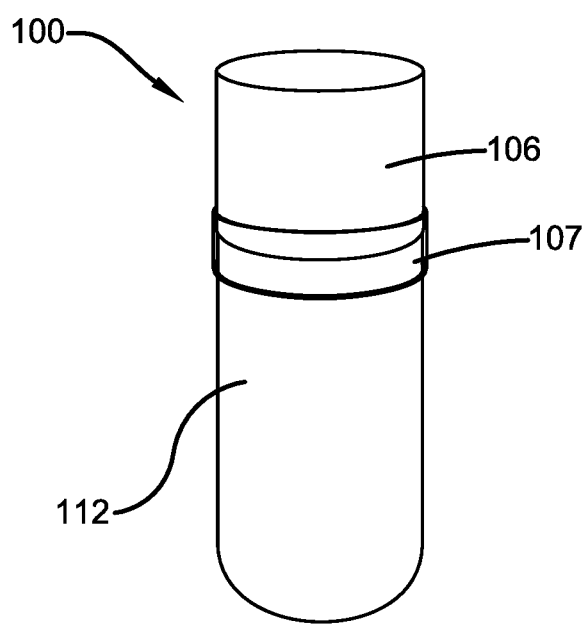
FIG. 6 illustrates a perspective view of one potential embodiment of the fogger disinfectant device of the present invention in accordance with the disclosed architecture in a stored condition.

FIG. 4 illustrates a partial perspective view of one potential embodiment of the nozzle 104 of the portable fogger disinfectant device 100 of the present invention in accordance with the disclosed architecture. More specifically, the nozzle 104 is surrounded by a curved portion 1020 which extends circumferentially around the area containing the nozzle, except for an open portion where a flap 108 is present. The nozzle cap 102 is securely connected to the collar portion 1122 of the cylinder 112. The nozzle 104 has an opening 110 through which the disinfecting solution 200, 300 is dispersed in the surroundings when the device 100 is activated.

The nozzle 104 may also include a screen or mesh 111 to control the droplet size of the disinfecting solution 200, 300, with the droplet size preferably ranging from about 5 microns to about 50 microns and having a predefined dispensing rate and an effective solution concentration of between 10 to 90%. Droplets sizes for use in the present invention that range between 5-50 microns (µm) in diameter have proven to be the most effective. Preferably, the droplet size is between 10 and 35 microns. Droplets of this size are ideal to tackle pathogens, vector carriers and other pests. In addition, the effective portions of the disinfecting formulation can be applied in concentrations ranging from 10-90%, with the remaining portions making up the propellant, stabilizers, drying agents or other non-treatment components, and more preferably from 30-80% and at flow rates of up to 0.52 quarts per minute (31.7 quarts per hour or nearly 8 gallons an hour).

Application of disinfectants, sanitizing solutions and biocides via aerosol or fogging can significantly reduce the number of viable infectious pathogens in a particular area. Foggers produce micro droplets that float in the air for approximately 10 minutes after application, reaching the most inaccessible parts of a room or area where conventional cleaning or spraying typically can't reach. The smaller the droplet, the longer the particles will remain airborne. About 1 ounce of disinfectant solution 200, 300 will typically cover around 1,000 cubic feet.

Also, based on research, it has been shown that a 10 second drying time allows the ethanol to kill microbes such as *Pseudomonas aeruginosa, E. coli, Pseudomonas aeruginosa, Pseudomonas aeruginosa*, etc. The drying elements may range in solution from between 0.5 to about 15% in solution, and preferably between 2 and 7%. Drying elements may be selected from a group comprised of a calcium sulfate, sodium sulfate, calcium chloride and magnesium sulfate.

FIG. 5 illustrates a partial perspective view of one potential embodiment of the nozzle 104 of the portable fogger disinfectant device 100 of the present invention in accordance with the disclosed architecture in the process of being activated by a user 500. More specifically, in order to release the disinfecting material 200, 300 and distribute the same comprehensively and evenly throughout a room or enclosed area, the user 500 will gently press downwardly on the flap 108 of the nozzle 104 in the direction 502 of the cylinder 112. Alternatively, the flap 108 may be programmed to disperse the disinfecting material 200, 300 at a specific time, or can be activated using a voice command through a smartphone application or a voice activated device such as Amazon Alexa® or Google's voice assistant.

When the flap 108 is pressed downwards 502, the nozzle 104 is pushed downwards and the disinfecting material 200, 300 is released as a spray 504 through the opening 110. After initiating use, the nozzle 104 is manually or automatically released, thereby allowing the disinfecting material 200, 300 to escape in a controlled manner. Once dispersed, the disinfecting material 200, 300 should be allowed to air dry, and the composition of the disinfecting material 200, 300 is such that it does not require the user 500 to wipe the surfaces on which the solution 200, 300 is dispersed. The amount of ethanol or other alcohol may be used to control the drying time of the solution 200, 300 from a few minutes to just seconds.

This versatile fogger device 100 of the present invention can be used on all hard surfaces (such as toilets, bins and sinks), soft surfaces (such as sofas, carpeting and mattresses), and the fragrant component of the disinfecting solution 200, 300 leaves a fresh fragrance in the air. The disinfectant device 100 is useful in killing 99.9% of all bacteria, viruses, germs, microbes and the like that it contacts including, without limitation, *E. coli* and *Salmonella* as well as cold and flu viruses.

FIG. 6 illustrates a perspective view of one potential embodiment of the fogger disinfectant device 100 of the present invention in accordance with the disclosed architecture in a stored condition. More specifically, the fogger disinfectant device 100 is presented with a cap 106 that covers the nozzle and the flap of the device 100 when not in use, thereby protecting the same from being damaged or inadvertently activated. The cylinder 112 of the fogger device 100 may be made available in different sizes and colors to accommodate different needs. Exact size, measurement, construction and design specifications of the fogger 100 of the present invention may vary upon manufacturing or the particular material that is used. Additionally, the cylinder 112 may have a name tag, name badges, laser-engraving, customizable colors and fonts, embroidery and prints.

Figure 7:
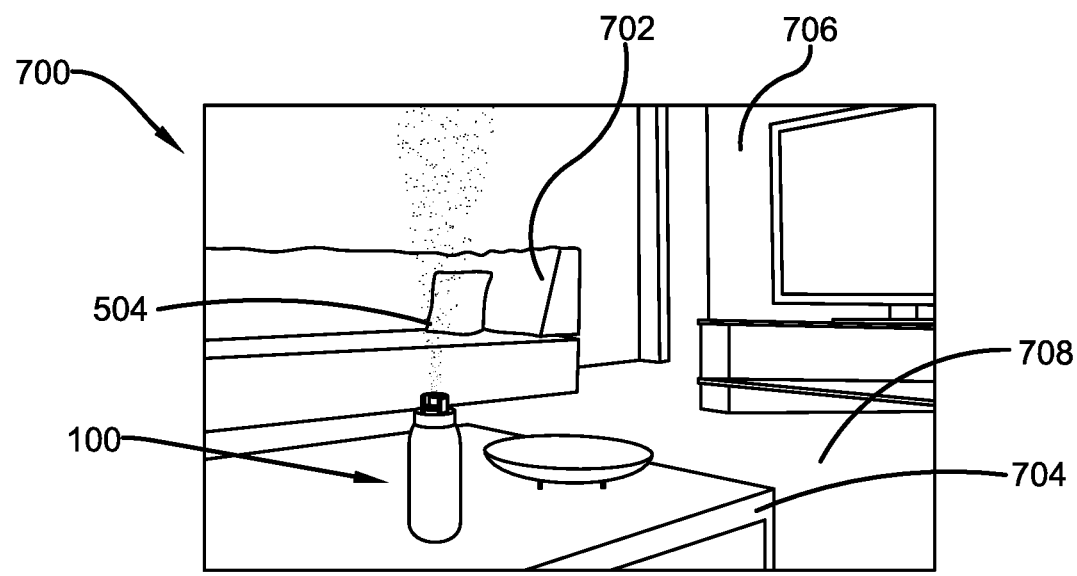
FIG. 7 illustrates an isometric view of a room with the portable fogger disinfectant product of the present invention placed therein and ready to use in accordance with the disclosed architecture.

FIG. 7 illustrates an isometric view of a room 700 with the portable fogger disinfectant device 100 of the present invention placed therein and ready to use in accordance with the disclosed architecture. More specifically, the room 700 may include, for example, a sofa 702, table 704, walls 706, ceiling, and floor 708. The fogger disinfectant device 100 is placed appropriately for use in a location that is substantially near the center of the room 700, and at a height calculated to allow the spray 504 that is dispersed therefrom to be able to fall onto or contact all of the various surfaces in the room 700, including those in hard to reach areas. In this manner, the disinfecting solution 200, 300 contacts all surfaces, walls and ceiling including the furniture and other items in the room 700, thereby disinfecting and sanitizing the room 700 without requiring one or more individuals to manually clean and disinfect the room 700. More specifically, the spray 504 is propelled outwardly and upwardly to a height near or at the ceiling and all walls of the room 700. The spray droplets then fall downward and impinge on succeeding upwardly propelled droplets. The net effect is a mushrooming or arching of the spray droplets 504 throughout the entire room, descending to contact all exposed surfaces.

Figure 8:
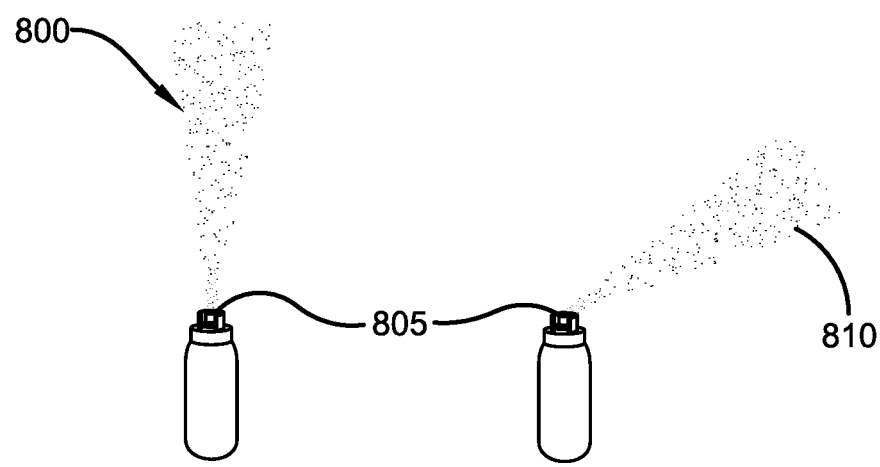
FIG. 8 illustrates a perspective view of two potential and differing spray patterns that may be achieved by the portable fogger disinfectant device of the present invention in accordance with the disclosed architecture.

FIG. 8 illustrates a perspective view of two potential and differing spray patterns 800, 810 that may be achieved by the portable fogger disinfectant device 100 of the present invention in accordance with the disclosed architecture. More specifically, the nozzle 805 can be set to achieve different spray patterns 800, 810, depending on the positioning of the fogger device. For example, the nozzle 805 and the opening in the curved portion 1020 could be positioned to allow the nozzle 805 to spray directionally versus upwardly.

In a further embodiment of the present invention, a method of quick disinfection of a room or an enclosed space is disclosed. More specifically, the method includes the initial step of acquiring a disinfecting fogger device 100 of sufficient capacity to disperse the disinfecting and sanitizing solution 200, 300 onto substantially all of the surfaces in a room 700. The fogger disinfectant device 100 is then placed substantially in the center of the room 700, and at a height that is appropriate for allowing the spray 504 to reach all surfaces in the room 700. Next, the nozzle 104 of the fogger device 100 is activated by pressing downwardly on the flap 108 present on the nozzle head 104. The fogger device 100 is allowed to discharge the disinfectant material 200, 300, and thereafter time is permitted for the disinfectant to contact the surfaces in the room 700. Finally, the room 700 is returned to productive use once the disinfectant solution has dried.

In an alternate embodiment of the present invention, a sensor module 109 may be present that may include one or more status sensors, such as a motion, heat source, temperature, humidity sensor or combinations thereof that prevent the device 100 from initiating while the sensor 109, for example, detects activity in the room 700. Further, a timing controller 113 can be programmed with a specific time duration as desired by the user to automatically release the disinfecting solution 200, 300 into the surroundings. In this manner, a user 500 would have time to vacate the room 700 before the dispersion beings. Nonetheless, the sensor 109 may override the timer 113 if, for example, the sensor 109 senses conditions that are not suitable or ideal for disinfection of the room 700.

In one embodiment, the cylinder 112 may contain 8 to 20 ounces or more of the disinfecting and sanitizing solution 200, 300. The expelled liquid droplets 504 are generally benign to all surfaces that they contact, whether made of fabric, wood, paint, paper, etc., and will not stain the same. The disinfecting and sanitizing solution 200, 300 will, however, disinfect and sanitize such surfaces. Ideally, the entire dispersal is accomplished in between one to five minutes, with the droplets drying upon contact. Thereafter, the user 50 may enter the room 700 to collect and dispose of the fogger device 100, and return the room 700 to productive use.

The fogger disinfectant device 100 of the present invention provides a means to evenly distribute a disinfectant throughout an enclosed area and thus mitigate odors, kill bacteria, eliminate fungi and destroy up to 99.9 percent of germs within the air. The opening 110 according to the present invention provides for vertical propulsion at a 360-degree angle therefore creating a fog type of a mist within the enclosed room where the fogger disinfectant 100 is used. A child safety seal may be inserted within the nozzle or on the packaging 107 to prevent the use of the device by a child. The safety seal may be an adhesive tape, shrink wrap film or other removable element.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "portable fogger disinfectant product", "fogger disinfectant", "fogger device", and "disinfectant fogger product" are interchangeable and refer to the fogger disinfectant product 100 of the present invention.

Notwithstanding the forgoing, the portable fogger disinfectant device 100 of the present invention can be of any suitable size and configuration as is known in the art without affecting the overall concept of the invention, provided that it accomplishes the above stated objectives. One of ordinary skill in the art will appreciate that the size, configuration and material of the portable fogger disinfectant device 100 as shown in the FIGS. are for illustrative purposes only, and that many other sizes of the portable fogger disinfectant device 100 are well within the scope of the present disclosure. Although the dimensions of the portable fogger disinfectant device 100 are important design parameters for user convenience, the portable fogger disinfectant device 100 may be of any size and shape that ensures optimal performance during use and/or that suits users need and/or preference.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A disinfecting device comprising;
   a canister for holding a content under a pressure that is greater than an ambient pressure, wherein the canister is comprised of a top, a bottom, a collar, a nozzle and a curved portion partially encompassing the nozzle, and further wherein the nozzle is disposed centrally of the collar and within the curved portion and comprises an actuator;
   a disinfecting solution;
   a propellant used to release the disinfecting solution held under pressure from the canister upon actuation of the nozzle;
   a cap which covers the nozzle, the collar and the curved portion; and
   a child safety seal insertable within the nozzle; and
   wherein the actuator is a flap that is both manually activatable and voice activatable to dispense the disinfecting solution.

2. The disinfecting device as recited in claim 1, wherein the nozzle comprises a screen to control a droplet size of the disinfecting solution upon dispersal.

3. The disinfecting device as recited in claim 1, wherein the nozzle may be set to disperse the disinfecting solution in a plurality of directions.

4. The disinfecting device as recited in claim 3, wherein a first direction of the plurality of direction is directionally oriented, and a second direction of the plurality of directions is upward to create a mushroom-like dispersal.

5. The disinfecting device as recited in claim 1, wherein the canister comprises a sensor for controlling a release of the disinfecting solution.

6. The disinfecting device as recited in claim 1, wherein the disinfecting solution comprises an ethanol, a compound having an alkyl group, an ammonium saccharinate, a quantity of water, and a fragrant oil.

7. The disinfecting device as recited in claim 1, wherein the disinfecting solution is comprised of an ethanol, a compound having an alkyl group comprised of C14, C12, and C16, a quantity of water, a fragrant oil, an ethanolamine, and an ammonium hydroxide.

8. The disinfecting device as recited in claim 6, wherein the disinfecting solution further comprises a drying element selected from a group including a calcium sulfate, a sodium sulfate, a calcium chloride and a magnesium sulfate, and further wherein the drying element may range in solution from between 0.5 to about 15%.

9. The disinfecting device as recited in claim 1, wherein the nozzle produces a disinfecting solution droplet size ranging between 5-50 microns in diameter.

10. The disinfecting device as recited in claim 9, wherein the disinfecting solution droplet size is between 10 and 35 microns in diameter.

11. The disinfecting device as recited in claim 2, wherein the nozzle comprises a second screen that is interchangeable with the screen to further control the droplet size.

* * * * *